US009622681B2

(12) United States Patent
Eichler et al.

(10) Patent No.: US 9,622,681 B2
(45) Date of Patent: Apr. 18, 2017

(54) METHOD AND SYSTEM ELIMINATING ELECTROMAGNETIC INTERFERENCE IN A MEDICAL IMAGE, IN REAL-TIME

(75) Inventors: Uzi Eichler, Haifa (IL); Eitan Oren, Haifa (IL)

(73) Assignee: MediGuide Ltd., Haifa (IL)

( * ) Notice: Subject to any disclaimer, the term of this patent is extended or adjusted under 35 U.S.C. 154(b) by 2420 days.

(21) Appl. No.: 11/815,154

(22) PCT Filed: Jan. 30, 2006

(86) PCT No.: PCT/IL2006/000119
§ 371 (c)(1),
(2), (4) Date: Jan. 23, 2008

(87) PCT Pub. No.: WO2006/080020
PCT Pub. Date: Aug. 3, 2006

(65) Prior Publication Data
US 2008/0319312 A1 Dec. 25, 2008

Related U.S. Application Data

(60) Provisional application No. 60/648,975, filed on Jan. 31, 2005.

(51) Int. Cl.
*A61B 5/05* (2006.01)
*A61B 5/06* (2006.01)
(Continued)

(52) U.S. Cl.
CPC ............... *A61B 5/06* (2013.01); *A61B 34/20* (2016.02); *A61B 90/36* (2016.02); *A61B 2034/2051* (2016.02)

(58) Field of Classification Search
USPC ....... 600/407, 410, 411, 413, 414, 420, 424, 600/426; 378/62, 63
See application file for complete search history.

(56) References Cited

U.S. PATENT DOCUMENTS 5,465,724 A * 11/1995 Sliwa et al. .................. 600/459
6,101,239 A * 8/2000 Kawasaki et al. .............. 378/63
(Continued)

FOREIGN PATENT DOCUMENTS

JP H01-126213 8/1989
JP H04-325142 11/1992
(Continued)

*Primary Examiner* — Rajeev Siripurapu
(74) *Attorney, Agent, or Firm* — Dykema Gossett PLLC

(57) ABSTRACT

In a medical apparatus including a medical imaging system and a medical position and navigation system (MPS), the medical imaging system including an imaging transmitter, periodically emitting imaging radiation and an imaging detector, the medical position and navigation system including at least one MPS transmitter periodically transmitting MPS radiation and at least one MPS detector, the MPS radiation electromagnetically interfering with at least one mode of operation of the imaging detector, a device for eliminating interference to the imaging detector caused by positioning radiation, the device comprising a synchronizer, coupled with the medical imaging system and with the medical position and navigation system, synchronizing the imaging detector and each the at least one MPS transmitter, so that neither of the at least one MPS transmitter transmits during the at least one mode of operation of the imaging detector.

14 Claims, 11 Drawing Sheets

(51) Int. Cl.
*A61B 90/00* (2016.01)
*A61B 34/20* (2016.01)

(56) References Cited

U.S. PATENT DOCUMENTS

| | | | |
|---|---|---|---|
| 6,122,538 | A * | 9/2000 | Sliwa et al. ............... 600/407 |
| 6,154,516 | A * | 11/2000 | Heuscher et al. ............ 378/15 |
| 6,304,769 | B1 | 10/2001 | Arenson et al. |
| 6,330,467 | B1 | 12/2001 | Creighton, IV et al. |
| 6,823,207 | B1 | 11/2004 | Jensen et al. |
| 2001/0049474 | A1* | 12/2001 | Wagshul ................... 600/411 |
| 2003/0135112 | A1 | 7/2003 | Ritter et al. |
| 2003/0153827 | A1 | 8/2003 | Ritter et al. |
| 2004/0068173 | A1 | 4/2004 | Viswanathan |
| 2004/0116803 | A1 | 6/2004 | Jascob et al. |
| 2005/0261571 | A1* | 11/2005 | Willis et al. ............... 600/411 |

FOREIGN PATENT DOCUMENTS

| | | |
|---|---|---|
| JP | 2002-272700 | 9/2002 |
| JP | 2004-533863 A | 11/2004 |
| JP | 2005-006790 | 1/2005 |
| WO | 02/064011 A2 | 8/2002 |
| WO | WO-02/074164 | 9/2002 |

\* cited by examiner

METHOD AND SYSTEM ELIMINATING ELECTROMAGNETIC INTERFERENCE IN A MEDICAL IMAGE, IN REAL-TIME

FIELD OF THE DISCLOSED TECHNIQUE

The disclosed technique relates to medical imaging in general, and to methods and systems for reducing electromagnetic interference in an image, obtained by a medical imaging system, in particular.

BACKGROUND OF THE DISCLOSED TECHNIQUE

Electromagnetic radiation medical imaging systems are known in the art. Such systems are generally used to create a representation in the form of an image of the anatomy of a region of interest of a patient. Such electromagnetic radiation medical imaging systems are, for example, X-ray, CT, MRI, US or PET systems.

Medical positioning systems (MPS) are known in the art. Such systems are generally used to track and mark the location of an object (e.g., catheter) in or around the body of a patient. Medical positioning systems may employ electromagnetic radiation to determine the location of a body in a reference coordinate system. More specifically, these systems employ the relationship between the strength of the signal associated with this radiation, as detected by a detector, and the distance of this detector from the source of the radiation. For example, such medical positioning systems may include three electromagnetic radiation transmitters, in the form of transmitting coils, positioned such that the axes normal to the plane crated by one of the turns of each coil are mutually orthogonal. These systems may employ detectors in the form of one or more receiving coils, positioned such that the axes, normal to the plane crated by one of the turns of each coil, are mutually orthogonal. Each coil corresponds to an axis in a reference coordinate frame.

A Medical imaging system may be employed in conjunction with a medical positioning system to obtain the image of the anatomy of a patient and the location of an object within or on the patient. For example, during a catheterization procedure, knowledge of the position of the catheter within the body of a patient, and an image of the anatomy of the region in which the catheterization procedure is performed, may be necessary.

Reference is now made to FIG. 1, which is a schematic illustration of a system, generally referenced 10, for navigating an object, such as a distal tip of a catheter, in conjunction with images of the anatomy of a portion of a body of a patient as, detected by a medical imaging system, which is known in the art. System 10 includes medical imaging system 28, a medical positioning system (MPS) 34, a catheter 16, a display unit 32 and a table 14. Medical imaging system 28 includes an imaging radiation transmitter 30 and an imaging radiation detector 26. Catheter 16 includes a distal end 18. Distal end 18 includes magnetic position radiation detectors (not shown). This position radiation detector may be a single coil detector or a multiple coil detector (not shown). The detector is operative for detecting magnetic fields. Medical positioning system 34 includes positioning radiation transmitters 20, 22 and 24. Positioning radiation transmitters 20, 22 and 24 are, for example, three coils.

Display unit 32 is coupled with imaging radiation detector 26. Positioning radiation transmitters 20, 22 and 24, and catheter 16 are coupled with medical positioning system 34.

Catheter 16 is inserted to a patient 12, subjected to a treatment, and navigated towards a region of interest (e.g., the cardiovascular system). Imaging radiation transmitter 30 transmits radiation that passes through patient 12. The radiation, detected by imaging radiation detector 26, is a representation of the anatomy of a region of interest of patient 12. An image representing the anatomy of the region of interest of patient 12 is formed on display unit 32. The image includes catheter 16 and distal end 18. Positioning radiation transmitters 20, 22 and 24 transmit magnetic fields which are mutually orthogonal, corresponding to axes of a reference coordinate frame. The detector at distal end 18 detects the magnetic fields generated by positioning radiation transmitters 20, 22 and 24. The detected signal is related to the position of distal end 18, for example, by the Biot Savart law, know in the art. Thus, the position of distal end 18 is obtained by medical positioning system 34. Positioning radiation transmitters 20, 22 and 24 are located on imaging radiation detector 26 so as to register the coordinate system associated with imaging radiation detector 26 and the coordinate system associated with MPS 34 and to maximize the signal to noise ration of the signals detected by the positioning radiation detector.

However, imaging radiation detector 26 acquires the imaging radiation transmitted by imaging radiation transmitter 30, concurrently with positioning radiation transmitter 20, 22 and 24. Thus, due to the proximity of the positioning radiation transmitters to the imaging radiation detector, the magnetic field generated thereby, may affect imaging radiation detector 26. Consequently the image formed on display unit 32 may be corrupted.

U.S. Pat. No. 6,810,110 to Pelc et al. entitled "X-Ray Tube for Operating in A Magnetic Field" is directed to a method wherein an x-ray source, including a cathode, an anode and magnetic means. The magnetic means produce a magnetic field having magnetic field lines passing from the cathode to the anode to compensate or correct an otherwise undesired magnetic field. The magnetic means may include an electromagnet or permanent magnets. The electromagnet may be electromagnetic windings or coils mechanically coupled to the x-ray source. The permanent magnets may be integrated inside or positioned outside of the x-ray source.

U.S. Pat. No. 6,828,728 to Levinson, entitled "Processing images for removal of artifacts" directs to a method wherein interference in an X-Ray image is removed by processing the image after the acquisition thereof. The method to Levinson, initially identify a region in the image, with a standard deviation below a predetermined threshold. This identified region is declared to be free of artifacts. In the next step, each pixel element, on the outer edges of the imaging sensor, starting from the initially identified region, is cleaned. Cleaning is achieved by testing each pixel in sequence and comparing its value with the two preceding clean neighbours in the respective row or column. If the tested pixel is determined not to have predetermined relationship with respect to these clean neighbours, it is replaced by a pixel value having a predetermined relationship with respect to the clean neighbours. In the last step, the remaining pixels are tested. If a pixel is found not to have a predetermined relationship with its neighbouring pixels, the pixel is replaced with the average value of the neighbouring pixels.

U.S. Pat. No. 6,118,848 to Simon et al. entitled "System and methods for the reduction and elimination of image artifacts in the calibration of X-ray imagers" directs to a method to reduce the representation of calibration markers present in an X-ray image. The representations of the calibration markers are reduced by replacing the pixels representing the calibration markers by pixels related to the pixels surrounding the representation of the calibration markers. The relationship between the surrounding pixels and the replaced pixels may be that of the average of the surrounding pixels or multiple regions averaging.

U.S. Pat. No. 6,314,310 to Ben-Haim et al., entitled "X-Ray Guided Surgical Location System with Extended Mapping Volume", is directed to a method for displaying anatomical features of interest in the body of a patient acquired by one or more X-ray images, with a probe, inserted into the body of the patient. The probe includes sensing devices such as magnetic field responsive coils for determining six-dimensional position and orientation coordinates. During the surgery, as the probe is advanced into the body of the patient, signals generated by the coils on the probe are used to track the coordinates of the tool and to update accordingly, the display showing the image of the tool and the patient. Preferably, a new X-ray image is acquired from time to time. According to the publication to Ben-Haim et al, a surgeon is able to insert and manipulate the probe in the body of the patient under the visual guidance of an X-ray image of the body that includes continuously-updated representation of the tool. The X-ray images is acquired during the surgical procedure and may be updated as desired.

SUMMARY OF THE PRESENT DISCLOSED TECHNIQUE

It is an object of the disclosed technique to provide a novel method and system for synchronizing a medical imaging system with a medical positioning system.

In accordance with the disclosed technique, there is thus provided a device for eliminating interference to an imaging detector caused by positioning radiation. A medical apparatus includes a medical imaging system and a medical position and navigation system (MPS). The medical imaging system includes an imaging transmitter, periodically emitting imaging radiation and an imaging detector. The medical position and navigation system (MPS) includes at least one MPS transmitter periodically transmitting MPS radiation and at least one MPS detector. The MPS radiation electromagnetically interferes with at least one mode of operation of the imaging detector. The device includes a synchronizer, coupled with the medical imaging system and with the medical position and navigation system. The synchronizer synchronizes the imaging detector and each the at least one MPS transmitter, so that neither of the at least one MPS transmitter transmits during the at least one mode of operation of the imaging detector.

In accordance with another embodiment of the disclosed technique, there is thus provided a combined imaging and positioning apparatus. The combine imaging a positioning apparatus includes a medical imaging system, a medical position and navigation system and a synchronizer. The synchronizer is coupled with the medical imaging system and with the medical position and navigation system. The medical imaging system obtains a representation of the anatomy of a portion of a body. The medical imaging system includes an imaging radiation transmitter for periodically transmitting imaging radiation and an imaging detector. The medical position and navigation system (MPS) includes at least one MPS transmitter for transmitting MPS radiation, the MPS radiation electromagnetically interferes with at least one mode of operation of the imaging detector. The medical position and navigation system (MPS) further includes and at least one MPS detector for detecting MPS radiation. The synchronizer, synchronizes the imaging detector and each the at least one MPS transmitter, so that neither of the at least one MPS transmitter transmits during the at least one mode of operation of the imaging detector.

In accordance with a further embodiment of the disclosed technique, there is thus provided a method for eliminating interference to an imaging detector caused by positioning radiation. A medical apparatus includes a medical imaging system and a medical position and navigation system (MPS). The medical imaging system includes an imaging transmitter and an imaging detector. The imaging transmitter periodically emits imaging radiation. The imaging detector periodically detects an image frame. The medical position and navigation system includes at least one MPS transmitter and at least one MPS detector. The MPS transmitter periodically transmits MPS radiation. The method includes the procedures of synchronizing the detection of image frames and the transmission of the MPS radiation, to be mutually exclusive in the time domain.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a method and a system to reduce the interference in real time images, acquired by a medical imaging system, caused by a magnetic field, generated by positioning radiation transmitters of a medical positioning system (MPS). According to the disclosed technique, a synchronizer synchronizes the operation of the imaging radiation detector of the medical imaging system and the medical positioning radiation transmitters (i.e., at least one mode of operation of the imaging radiation detector and the operation of the positioning radiation transmitters are mutually exclusive in time). As a result of this synchronization, the positioning radiation transmitters do not transmit positioning radiation while imaging radiation detector acquires imaging radiation. (i.e., the operations of acquiring an image and transmitting positioning radiation are mutually exclusive in time). According to another embodiment of the disclosed technique, the position radiation transmitters do not transmit while the medical imaging system samples the acquired image frame from the imaging radiation detector (i.e., the operations of sampling an image frame and transmitting positioning radiation are mutually exclusive in time). During the image frame sampling period the medical imaging system samples the pixel values accumulated in the imaging radiation detector during the image acquisition period.

Additionally, the imaging radiation detector is electromagnetically shielded with metal plates to prevent the magnetic filed interference with the electronics thereof. Consequently, the interferences of the magnetic fields with the imaging radiation detector and the imaging radiation transmitter, is eliminated. Thus, the imaging system produces real time images, which does not exhibit visible flaws due to magnetic field interference caused by the proximity of the positioning radiation transmitter to the imaging radiation detector.

Figure 1:
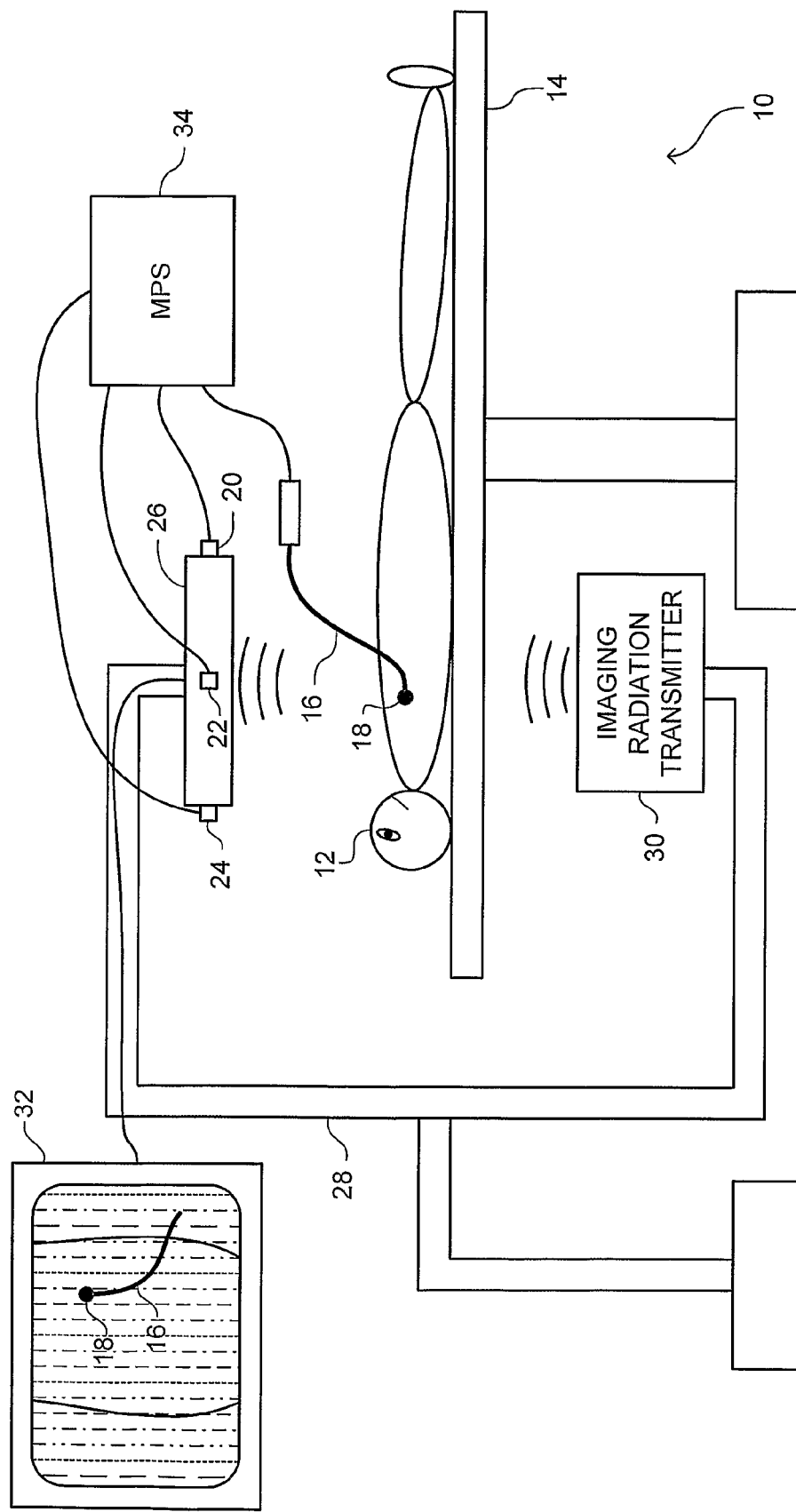
FIG. 1 is a schematic illustration of a system, for navigating an object, such as a distal tip of a catheter, in conjunction with images of the anatomy of a portion of a body of a patient as detected by a medical imaging system, which is known in the art.
Figure 2:
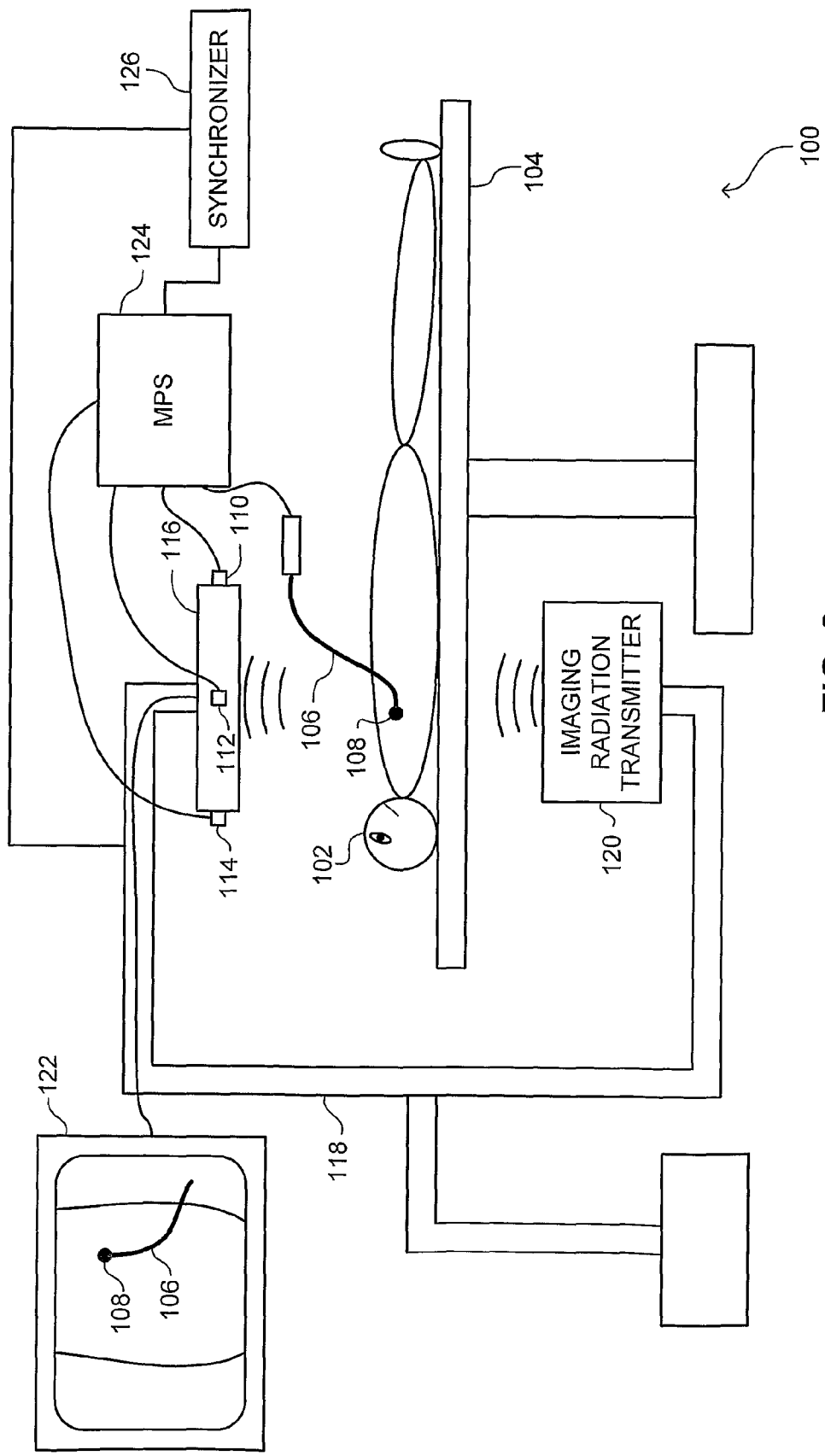
FIG. 2 is a schematic illustration of a system, for navigating an object such as a distal tip of a catheter in conjunction with images of the anatomy of a portion of a body of a patient as detected by a medical imaging system, constructed and operative in accordance with an embodiment of the disclosed technique.

Reference is now made to FIG. 2, which is a schematic illustration of a system, generally referenced 100, for navigating an object such as a distal tip of a catheter in conjunction with images of the anatomy of a portion of a body of a patient as detected by a medical imaging system, constructed and operative in accordance with an embodiment of the disclosed technique. System 100 includes a medical imaging system 118, an MPS 124, a catheter 106, a synchronizer 126 and a table 104. Medical imaging system 118 includes an imaging radiation transmitter 120, an imaging radiation detector 116 and a display unit 122. MPS 124 includes positioning radiation transmitters 110, 112 and 114 and a position radiation detector (not shown), operative for detecting magnetic fields, fitted on catheter 106. Positioning radiation transmitters 110, 112 and 114 are, for example, three coils, positioned such that the axes, normal to the plane crated by one of the turns of the coils, are orthogonal. Catheter 106 includes a distal end 108. Distal end 108 includes positioning radiation detectors, (e.g., a single axis coil or multiple axes coils).

Display unit 122 is coupled with medical imaging system 118. Positioning radiation transmitters 110, 112 and 114, and the position radiation detector (not shown) fitted on tip 108 of catheter 106 are coupled with MPS 124. Synchronizer 126 is coupled to medical imaging system 118 and MPS 124.

Catheter 106 is inserted to a patient 102, subjected to a treatment, and navigated toward a region of interest (e.g., the cardiovascular system). Imaging radiation transmitter 120 transmits radiation that passes through patient 102. Imaging radiation detector 116 detects an image frame. This detection includes two modes. The first mode is acquiring the imaging radiation and the second mode is sampling the acquired pixel values accumulated in the imaging radiation detector during the image acquisition period. This acquired radiation, detected by imaging radiation detector 116, is a representation of the anatomy of a region of interest of patient 102 in an image coordinate system. An image representing the anatomy of the region of interest of patient 102 is formed on display unit 122. This image includes catheter 106 and distal end 108. Positioning radiation transmitters 110, 112 and 114 transmit magnetic fields which are mutually orthogonal, corresponding to an MPS coordinate system. The position detector at the distal end 18 detects the magnetic fields generated by positioning radiation transmitters 110, 112 and 114. Synchronizer 126 enables positioning radiation transmitters 110, 112 and 114 to transmit when imaging radiation detector 116 does not acquire imaging radiation. Synchronizer 126 disables transmitters 110, 112 and 114 (i.e., at least from transmitting) when imaging radiation detector 116 acquires imaging radiation. According to another embodiment of the disclosed technique, synchronizer 126 enables positioning radiation transmitters 110, 112 and 114 to transmit when medical imaging system 118 does not sample the acquired image from image radiation detector 116. Synchronizer 126 disables transmitters 110, 112 and 114 (i.e., at least from transmitting) when medical imaging system 118 samples the acquired image from image radiation detector 116.

Figure 3:
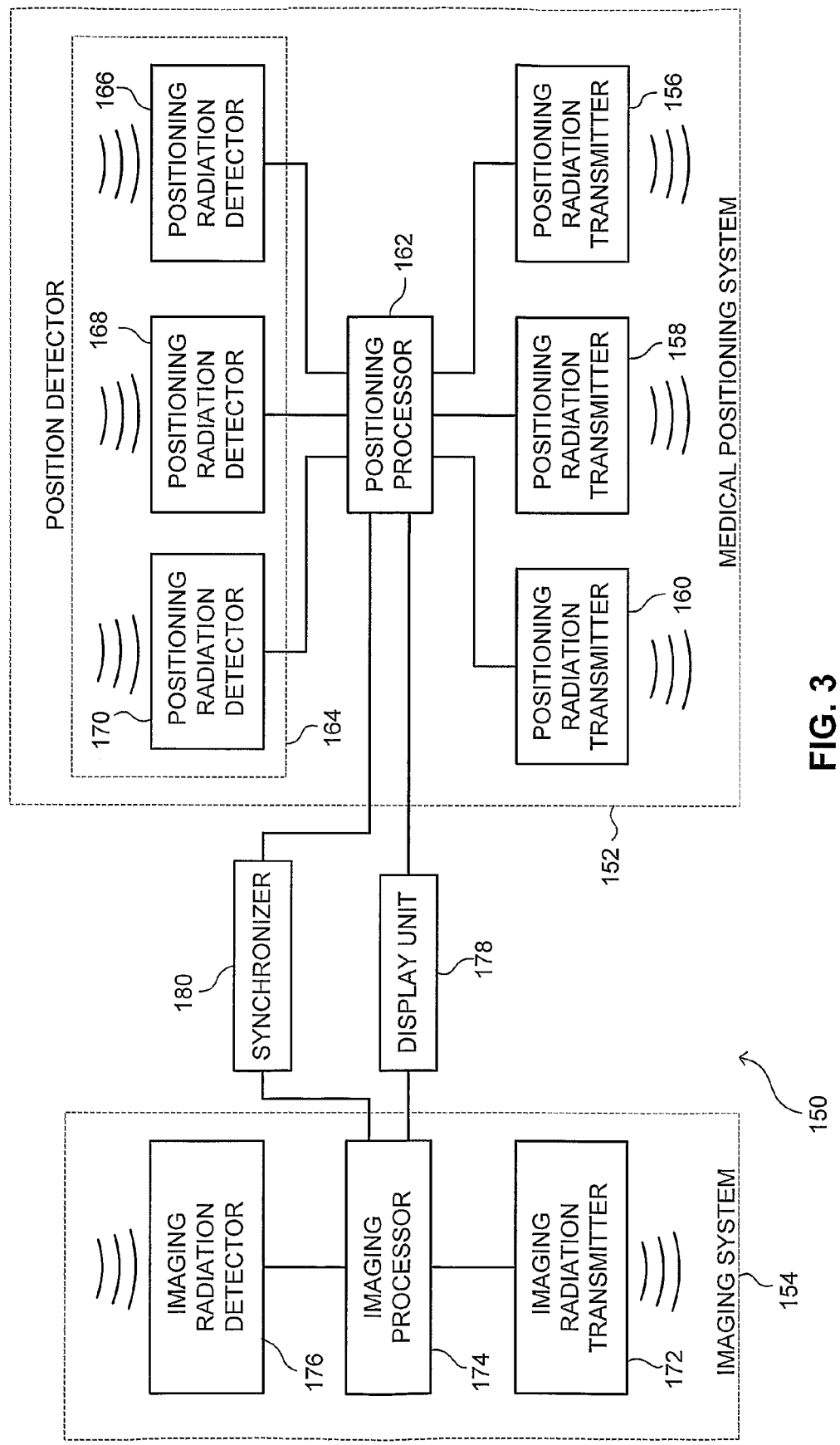
FIG. 3 is a schematic illustration of a system, for navigating an object such as a distal tip of a catheter, in conjunction with images of the anatomy of a portion of a body of a patient, as detected by a medical imaging system, constructed and operative in accordance with another embodiment of the disclosed technique.

Reference is now made to FIG. 3, which is a schematic illustration of a system, generally referenced 150, for navigating an object such as a distal tip of a catheter, in conjunction with images of the anatomy of a portion of a body of a patient, as detected by a medical imaging system, constructed and operative in accordance with a further embodiment of the disclosed technique. System 150 includes a MPS 152, a medical imaging system 154, a display unit 178 and a synchronizer 180. MPS 152 includes a position detector 164, positioning radiation transmitters 156, 158, 160 and positioning processor 162. Each of position radiation transmitters 156, 158 and 160 may be a group of transmitters. These transmitters may transmit at mutually exclusive frequencies or mutually exclusive time periods. Position detector 164 includes positioning radiation detectors 166, 168 and 170. Alternatively, position detector 164 may include a single position radiation detector. Medical imaging system 154 includes imaging radiation transmitter 172, imaging radiation detector 176 and imaging processor 174.

Synchronizer 180 and display unit 178 are coupled with imaging system 154 and with MPS 152. Positioning processor 162 is coupled with position detector 164, with positioning radiation transmitters 156, 158, and 160, with display unit 178 and with synchronizer 180. Imaging processor 174 is coupled with imaging radiation detector 176, with imaging radiation transmitter 178, with display unit 178 and with synchronizer 180. An object such as a catheter (not shown) is inserted to a patient (not shown) subjected to a treatment, and navigated toward a region of interest (e.g., the cardiovascular system).

Imaging radiation transmitter 172 emits radiation that passes through the patient. Imaging radiation detector 176 detects an image frame. This detection includes two modes of operation. The first mode is acquiring the imaging radiation and the second mode is sampling the acquired pixel values accumulated in the imaging radiation detector during the image acquisition period. This radiation, acquired by imaging radiation detector 176, is a representation of the anatomy of a region of interest of the patient. Image detector 176 samples the acquired pixel values of the acquired imaging radiation. An image representing the anatomy of the region of interest of the patient is formed on display unit 178. The image includes the catheter. Positioning radiation transmitters 156, 158 and 160 transmit magnetic fields which are mutually orthogonal, corresponding to an MPS coordinate system. Positioning detector 164, detect the magnetic fields generated by positioning radiation transmitters 156, 158 and 160. The detected signals are related to the position of the distal end of the catheter in relation to positioning radiation transmitters 156, 158, 160. When the positioning radiation transmitters 156, 158, 160 are mounted on the imaging radiation detector 174, the coordinates system, associated with the MPS, is registered with the coordinates system associated with imaging system. Synchronizer 178 enables positioning radiation transmitters 156, 158, and 160 to transmit when imaging radiation detector 174 does not acquire imaging radiation. Synchronizer 178 disables transmitters 156, 158, and 160 when imaging radiation detector 174 acquires imaging radiation. According to another embodiment of the disclosed technique, synchronizer 180 enables the positioning radiation transmitters 156, 158, and 160 to transmit when medical imaging system 154 does not sample the acquired image. Synchronizer 180 disables transmitters 156, 158, and 160 when medical imaging system samples the acquired image.

Consequently, the interferences, caused by the magnetic fields, with imaging radiation detector 176, are eliminated. Thus, medical imaging system 154 produces an image, which does not exhibit visible flaws due to magnetic field interference caused by the proximity of positioning radiation transmitters 156, 158 and 160 to imaging radiation detector 176.

Figure 4:
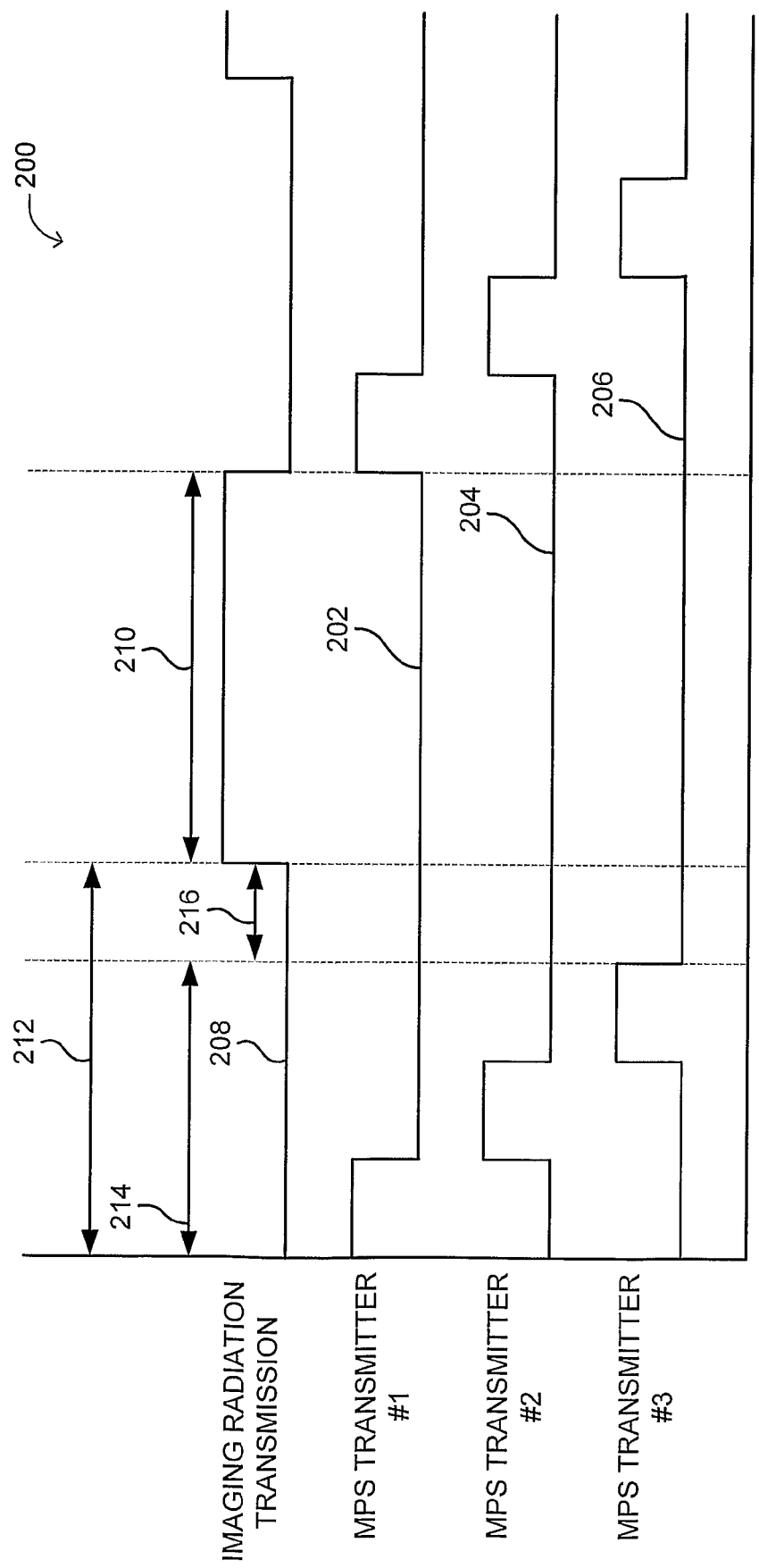
FIG. 4 is a schematic illustration of a timing diagram, in accordance with a further embodiment of the disclosed technique.

Reference is now made to FIG. 4 which is a schematic illustration of a timing diagram generally referenced 200, in accordance with a further embodiment of the disclosed technique. Timing diagram 200 includes signals 202, 204, 206 and 208. Signal 208 is the timing signal associated with the transmission of imaging radiation by imaging radiation transmitter 172 (FIG. 3). Signals 202, 204 and 206 are the timing signals associated with the operation of positioning radiation transmitters 156, 158 and 160 (FIG. 3) respectively. Transmitters 156, 158 and 160 (FIG. 3) are operated sequentially so as to enable the detection of the position (and orientation) of an object, with respect to each axis of a reference coordinate frame, independently. Alternatively, positioning radiation transmitters 156, 158 and 160 may be operated concurrently but at different frequencies.

Time period 210 is the imaging radiation transmission period. During the imaging radiation transmission period the imaging radiation transmitter transmits imaging radiation. Time period 212 is the imaging radiation non-transmission period. During the imaging radiation non-transmission period the imaging radiation transmitter does not transmit imaging radiation. Time period 214 is the positioning radiation transmission period. During the positioning radiation transmission period the positioning radiation transmitters transmit positioning radiation. Time period 216 is the relative phase range. The relative phase range is the range in which the phase of either the positioning radiation transmission period or the position radiation transmission period may change without the two transmission periods overlapping. The relative phase is defined as the difference between the imaging radiation non-transmission period and the positioning radiation transmission period.

During time period 210, imaging radiation detector 176 (FIG. 3) acquires imaging radiation. However, during time period 210, synchronizer 180 (FIG. 3) at least disables positioning radiation transmitters 156, 158 and 160 (FIG. 3) from transmitting. Consequently, the image obtained by imaging radiation detector 176 (FIG. 3) does not exhibit visible flaws due to magnetic field interference.

According to another embodiment of the disclosed technique, MPS may employ more than three magnetic field transmitters. However, not all the magnetic field transmitters can be activated during the imaging radiation detector non-acquisition period. Thus, the synchronizer prevents the positioning radiation transmitters from transmitting during the period in which the imaging radiation detector acquires radiation, and continues after the imaging radiation detector stops acquiring radiation.

Figure 5:
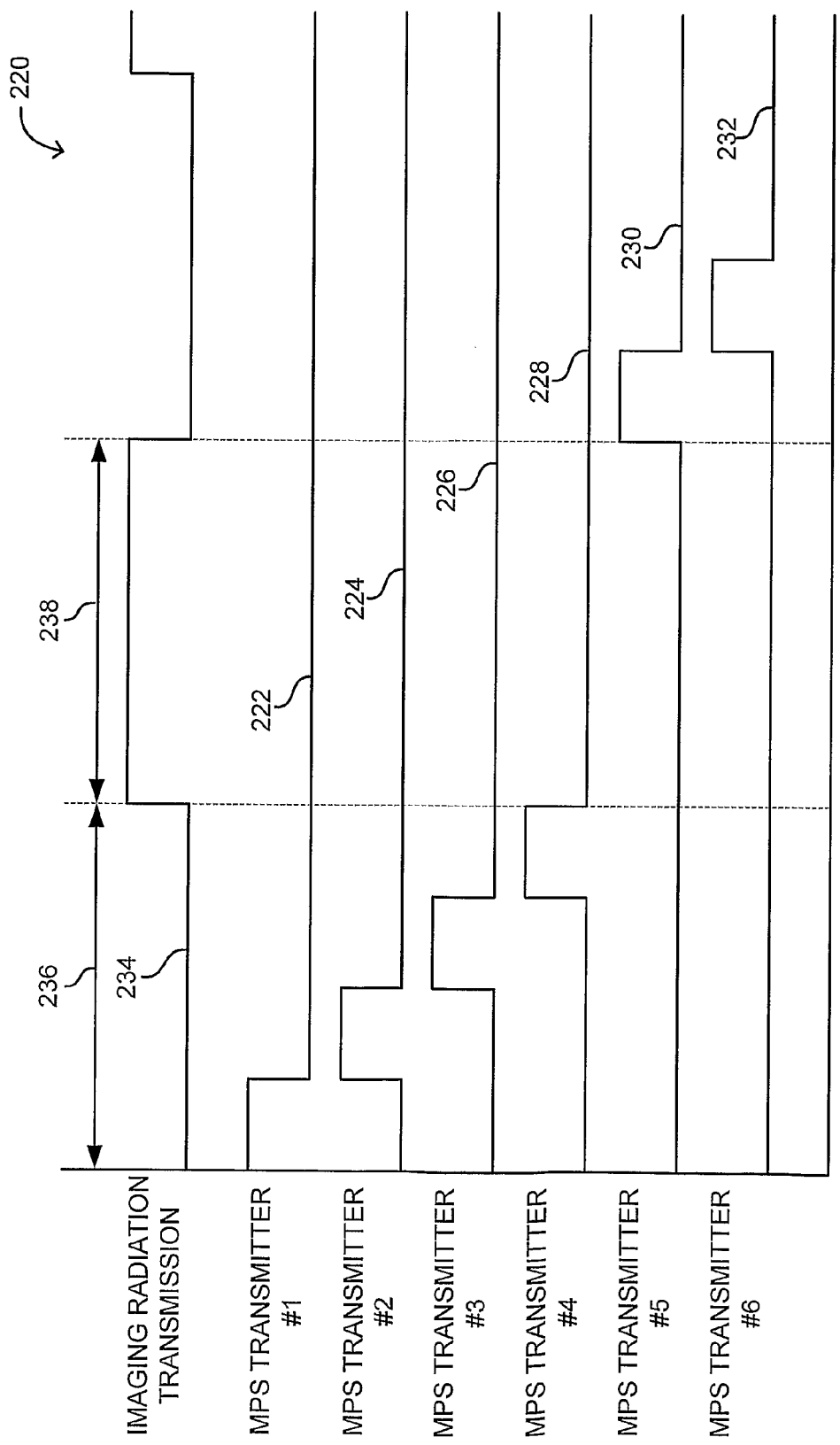
FIG. 5 is a schematic illustration of a timing diagram, in accordance with another embodiment of the disclosed technique.

Reference is now made to FIG. 5, which is a schematic illustration of timing diagram generally referenced 220 in accordance with a further embodiment of the disclosed technique. In Timing diagram 220, six positioning radiation transmitters are employed by the MPS. Timing diagram 220 includes signals 222, 224, 226, 228, 230, 232 and 234. Signal 222, 224, 226, 228, 230 and 232 are the timing signals associated with the operation of the positioning radiation transmitters. Signal 234 is associated with the operation of the imaging radiation transmitter 172 (FIG. 3). During time period 236 imaging radiation transmitter does not transmit imaging radiation. Thus, the positioning radiation transmitters can transmit. However, time period 236 is sufficient to operate only positioning radiation transmitters number 1, 2, 3 and 4. During time period 238, imaging radiation transmitter transmits radiation and the synchronizer disables the positioning radiation transmitters from transmitting. However, after the imaging radiation transmitter stops transmitting radiation, the synchronizer enables positioning radiation transmitters to transmit, starting from positioning radiation transmitter number 5.

Figure 6:
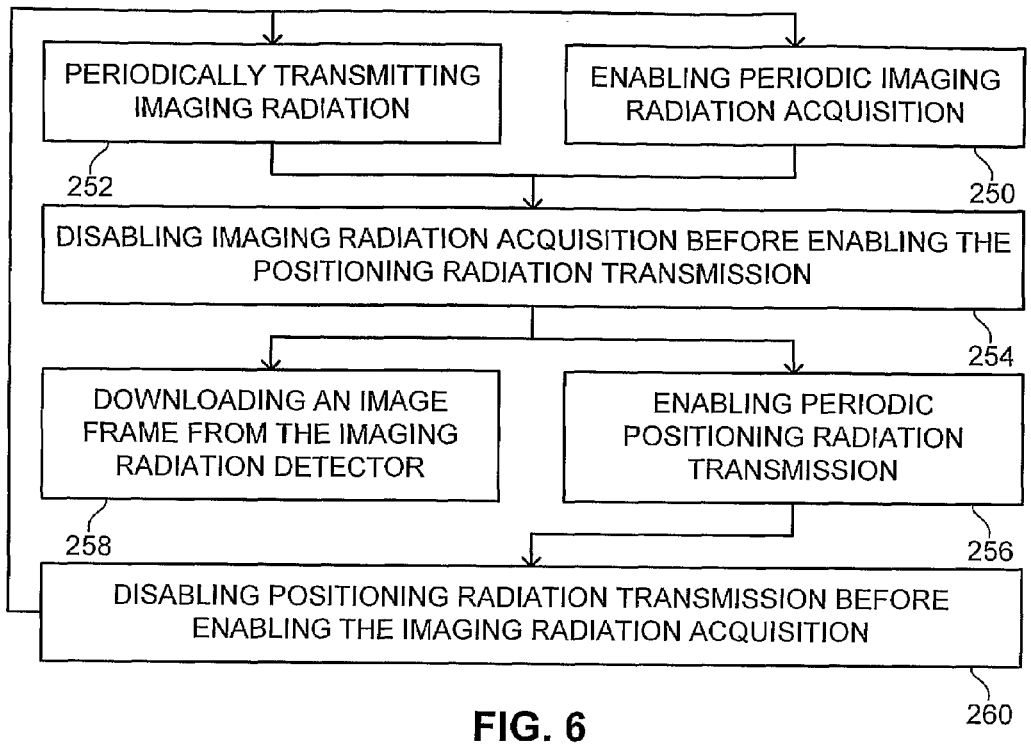
FIG. 6 is a schematic illustration of a method for synchronizing a medical imaging system with a medical positioning system, operative in accordance with a further embodiment of the disclosed technique.

Reference is now made to FIG. 6, which is a schematic illustration of a method for synchronizing a medical imaging system with a MPS, operative in accordance with a further embodiment of the disclosed technique. In procedure 250, the periodic imaging radiation acquisition is enabled. With reference to FIG. 3, synchronizer 180 enables periodic image acquisition and imaging radiation detector 176 acquires imaging radiation.

In procedure 252, imaging radiation is periodically transmitted while imaging radiation acquisition is enabled. With reference to FIG. 3, image radiation transmitter 172 periodically transmits imaging radiation. After procedures 250 and 252, the method proceeds to procedure 254.

In procedure 254, imaging radiation acquisition is disabled before enabling the positioning radiation transmission. With reference to FIG. 3, synchronizer 180 disables the imaging radiation transmission before enabling the positioning radiation transmission.

In procedure 256, periodic positioning radiation transmission is enabled. With reference to FIG. 3, synchronizer 180 enables the periodic positioning radiation transmission. After procedure 256, the method proceeds to procedure 260.

In procedure 258, an image frame is downloaded form the imaging radiation detector while the positioning radiation transmission is enabled. The image frame forms an image on the display unit. With reference to FIG. 3, imaging processor 174 downloads an image frame from imaging radiation detector 176.

In procedure 260, positioning radiation transmission is disabled before enabling imaging radiation acquisition. With reference to FIG. 3, synchronizer 180 disables the positioning radiation transmission before enabling the imaging radiation transmission. After procedure 260, the method proceeds to procedures 250 and 252.

According to another embodiment of the disclosed technique, two distinct (and may be different), preferably non-overlapping, periods, of the imaging acquisition and the positioning radiation, may overlap due to a drift in the relative phase between the two transmission periods. For example, with reference to FIG. 4, imaging radiation transmission period 210 may drift toward positioning radiation transmission period 212. The relative phase drift may be larger than the relative phase range 216. Thus an overlap between period 210 and period 212 will occur. The synchronizer delays the transmission of either the imaging radiation or the positioning radiation.

Figure 7:
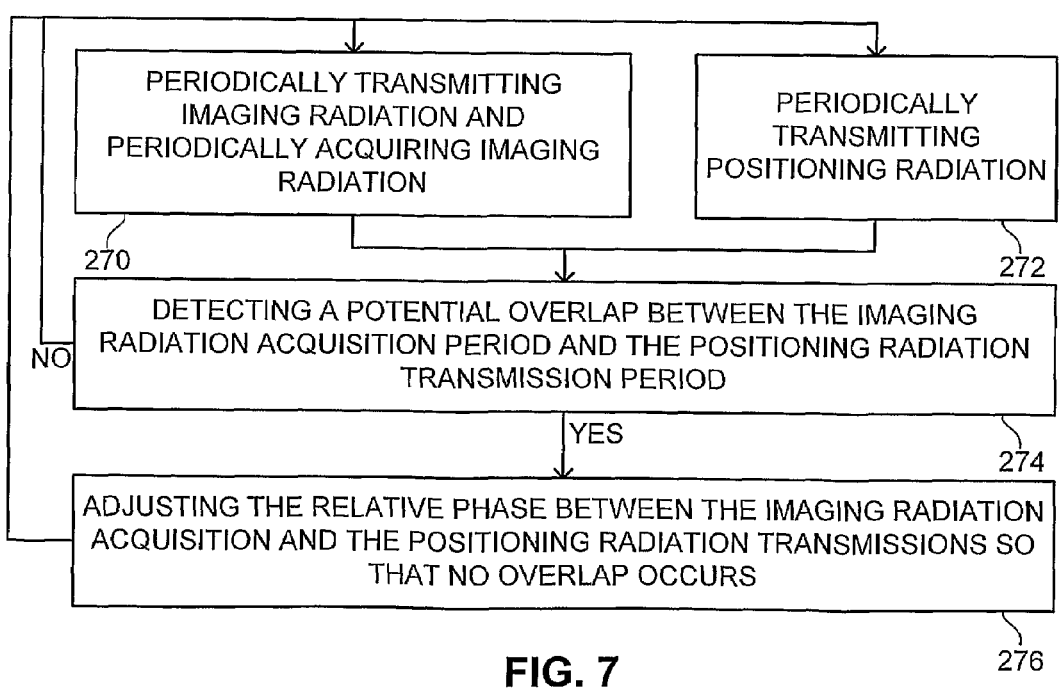
FIG. 7 is a schematic illustration of a method for synchronizing a medical imaging system with a medical positioning system, operative in accordance with another embodiment of the disclosed technique.

Reference is now made to FIG. 7, which is a schematic illustration of a method for synchronizing the operation of a MPS with a medical imaging system, operative in accordance with another embodiment of the disclosed technique. In procedure 270, imaging radiation is periodically transmitted and imaging radiation is periodically acquired. With reference to FIG. 3, imaging radiation transmitter 172 periodically transmits imaging radiation and imaging radiation detector 176 periodically acquires imaging radiation.

In procedure 272, positioning radiation is periodically transmitted while imaging radiation is acquired and while imaging radiation is periodically transmitted. The positioning radiation transmission period and the imaging radiation acquisition period are distinct and may be different. With reference to FIG. 3, positioning radiation transmitters 156, 158, and 160 periodically transmit positioning radiation. After procedures 270 and 272, the method proceeds to procedure 274.

In procedure 272, a potential overlap between the imaging radiation acquisition period and the positioning radiation transmission period is detected. This potential overlap is detected according to a change in the relative phase between the two periods. The relative phase is defined as the difference between the imaging radiation non-acquisition period and the positioning radiation transmission period. With reference to FIG. 4, the relative phase range 216 is the relative phase range in which the phase of either the imaging radiation acquisition period or the positioning radiation transmission period may change without the two transmission periods overlapping. When the combined relative phase drift of the imaging radiation acquisition period and the positioning radiation transmission period is larger than the relative phase range, then a potential overlap is detected and the method proceeds to procedure 276. When the relative phase drift of the imaging radiation acquisition period and the positioning radiation transmission period is at most equal to the relative phase range, then no potential overlap is detected and the method proceeds to procedures 270 and 272. With reference to FIG. 3, synchronizer 180 detects a potential overlap between the imaging radiation acquisition period and the positioning radiation transmission period.

In procedure 276, the relative phase between the imaging radiation acquisition and the positioning radiation transmission is adjusted so that no overlap occurs. With reference to FIG. 3, synchronizer 180 adjusts the relative phase between the imaging radiation acquisition and the positioning radiation transmission. After procedure 278, the method proceeds to procedure 270 and 272.

Figure 8:
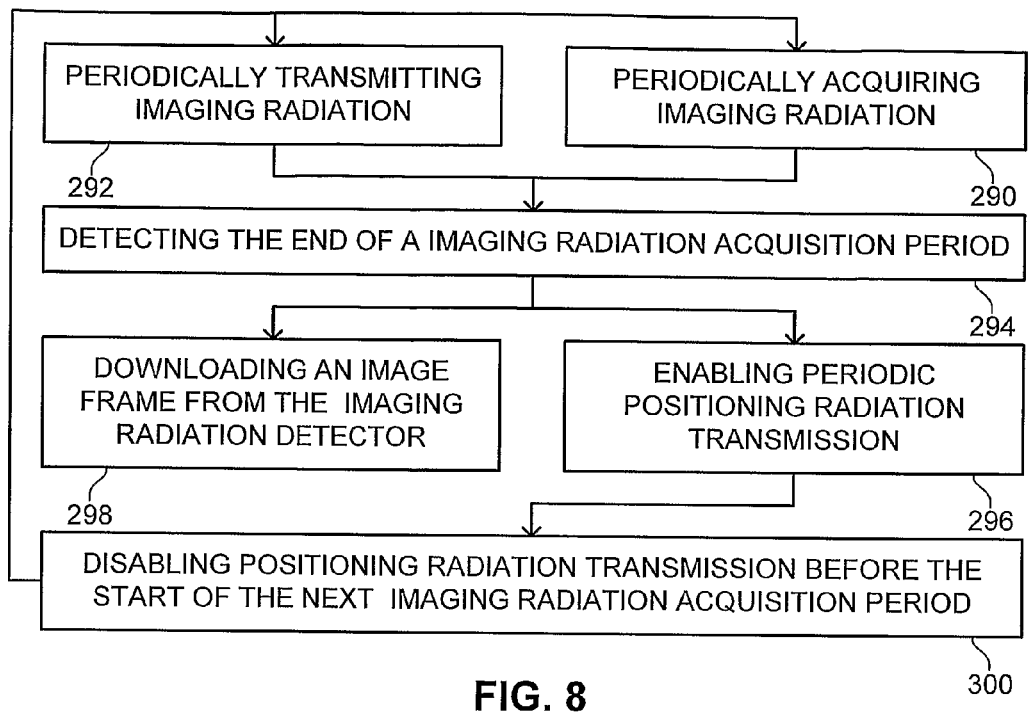
FIG. 8 is a schematic illustration of a method for synchronizing a medical imaging system with a medical positioning system, operative in accordance with a further embodiment of the disclosed technique.

According to a further embodiment of the disclosed technique, the synchronizer enables the transmission of the positioning radiation when the end of an imaging radiation acquisition period is detected. Reference is now made to FIG. 8, which is a schematic illustration of a method for synchronizing the operation of a MPS with a medical imaging system, operative in accordance with a further embodiment of the disclosed technique. In procedure 290, the imaging radiation is periodically acquired. With reference to FIG. 3, imaging radiation detector 176 periodically acquires imaging radiation.

In procedure 290, imaging radiation is periodically transmitted while imaging radiation is periodically acquired. With reference to FIG. 3, imaging radiation transmitter 172 periodically transmits imaging radiation. After procedures 290 and 292, the method proceeds to procedure 294.

In procedure 294, the end of an imaging radiation acquisition period is detected. With reference to FIG. 3, synchronizer 180 detects the end of the imaging radiation acquisition period.

In procedure 296, periodic positioning radiation transmission is enabled. With reference to FIG. 3, synchronizer 180 enables the periodic positioning radiation transmission. After procedure 296, the method proceeds to procedure 298.

In procedure 298, an image frame is downloaded form the imaging radiation detector while the position radiation transmission is enabled. The image frame forms an image on the display unit. With reference to FIG. 3, imaging processor 174 downloads an image frame from imaging radiation detector 176.

In procedure 300, positioning radiation transmission is disabled before the next imaging radiation acquisition period. With reference to FIG. 3, synchronizer 180 disables the positioning radiation transmission before the next imaging radiation acquisition period. After procedure 300, the method proceeds to procedures 290 and 292.

Figure 9:
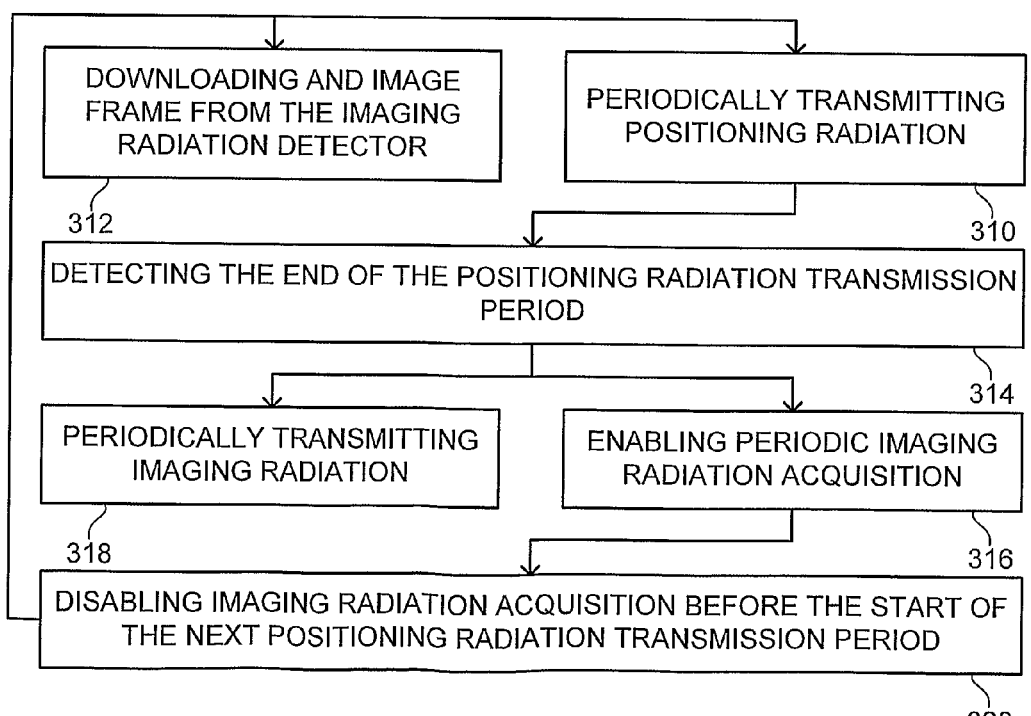
FIG. 9 is a schematic illustration of a method for synchronizing a medical imaging system with a medical positioning system, operative in accordance with another embodiment of the disclosed technique.

According to another embodiment of the disclosed technique, the synchronizer enables image acquisition when the positioning radiation transmission is disabled. Reference is now made to FIG. 9, which is a schematic illustration of a method for synchronizing the operation of a MPS with a medical imaging system, operative in accordance with another embodiment of the disclosed technique. In procedure 310, positioning radiation is transmitted periodically. With reference to FIG. 3, positioning radiation transmitters 156, 158 and 160 periodically transmit positioning radiation. After procedure 310, the method proceeds to procedure 314.

In procedure 312, an image frame is downloaded form the imaging radiation detector while positioning radiation is transmitted. The image frame forms an image on the display unit. With reference to FIG. 3, imaging processor 174 downloads an image frame from imaging radiation detector 174.

In procedure 314, the end of a positioning radiation transmission period is detected. With reference to FIG. 3, synchronizer 180 detects the end of a positioning radiation transmission period.

In procedure 316, periodic imaging radiation acquisition is enabled. With reference to FIG. 3, synchronizer 180 enables the periodic imaging radiation acquisition. After procedure 316, the method proceeds to procedure 320.

In procedure 318, the imaging radiation is periodically transmitted while imaging radiation acquisition is enabled. With reference to FIG. 3, imaging radiation transmitter 172 periodically transmits imaging radiation.

In procedure 320, imaging radiation acquisition is disabled before the start of the next positioning radiation transmission period. With reference to FIG. 3, synchronizer 180 disables the imaging radiation acquisition before the next positioning radiation transmission period. After procedure 320, the method proceeds to procedures 310 and 312.

Figure 10:
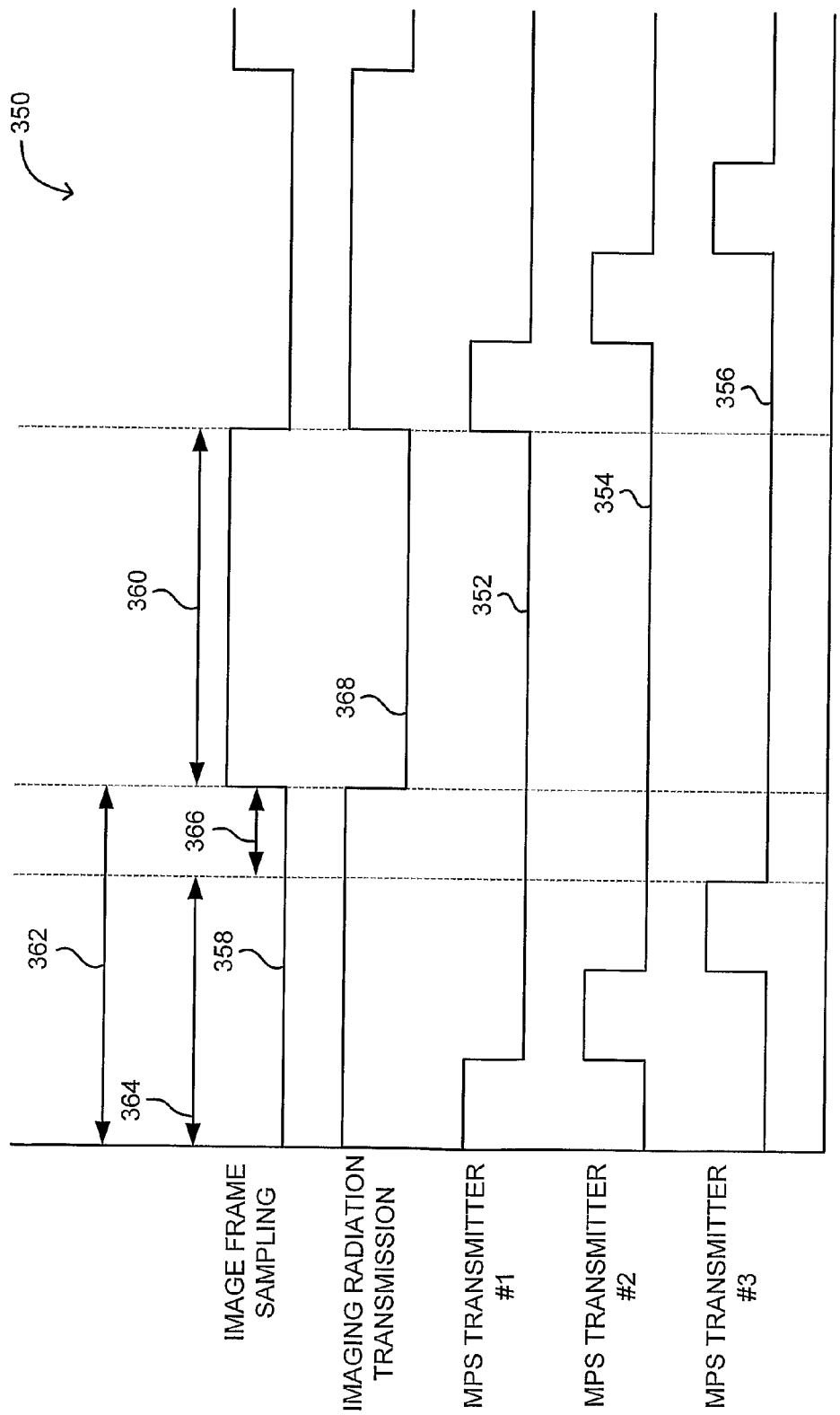
FIG. 10 is a schematic illustration of a timing diagram, in accordance with a further embodiment of the disclosed technique.

Reference is now made to FIG. 10 which is a schematic illustration of a timing diagram generally referenced 350, in accordance with a further embodiment of the disclosed technique. Timing diagram 350 includes signals 352, 354, 356, 358 and 368. Signal 358 is the timing signal associated with the image frame sampling. Signals 352, 354 and 356 are the timing signals associated with the operation of positioning radiation transmitters 156, 158 and 160 (FIG. 3) respectively. Signal 368 is the timing signal associated with the transmission of imaging radiation by imaging radiation transmitter 172 (FIG. 3) Transmitters 156, 158 and 160 (FIG. 3) are operated sequentially so as to enable the detection of the position (and orientation) of an object, with respect to each axis of an MPS coordinate system, independently. Alternatively, positioning radiation transmitters 156, 158 and 160 may be operated concurrently but at different frequencies. Time period 360 is the image frame sampling period. During time period 360 the medical imaging system samples the pixel values accumulated in the imaging radiation detector during the image acquisition period. During time period 360 the medical imaging system does not transmit imaging radiation. Time period 362 is the imaging radiation transmission period. During the imaging radiation transmission period the medical imaging system does not sample the accumulated pixel values. Time period 364 is the positioning radiation transmission period. During period 364 the positioning radiation transmitters transmit positioning radiation. Time period 366 is the relative phase range. The relative phase range is the range in which the phase of either the image frame sampling period or the position radiation transmission period may change without the two transmission periods overlapping. The relative phase is defined as the difference between the image frame non-sampling period and the positioning radiation transmission period.

During time period 360, medical imaging system 154 (FIG. 3) samples an image frame. However, during time period 360, synchronizer 180 (FIG. 3) at least disables positioning radiation transmitters 156, 158 and 160 (FIG. 3) from transmitting. Consequently, the image sampled by medical imaging system 154 (FIG. 3) does not exhibit visible flaws due to magnetic field interference.

According to another embodiment of the disclosed technique, MPS may employ more than three magnetic field transmitters. However, not all the magnetic field transmitters can be activated during the image frame non-sampling period. Thus, the synchronizer prevents the positioning radiation transmitters from transmitting during the period in which the medical imaging system samples an image frame, and continues after the medical imaging system stops sampling an image frame.

Figure 11:
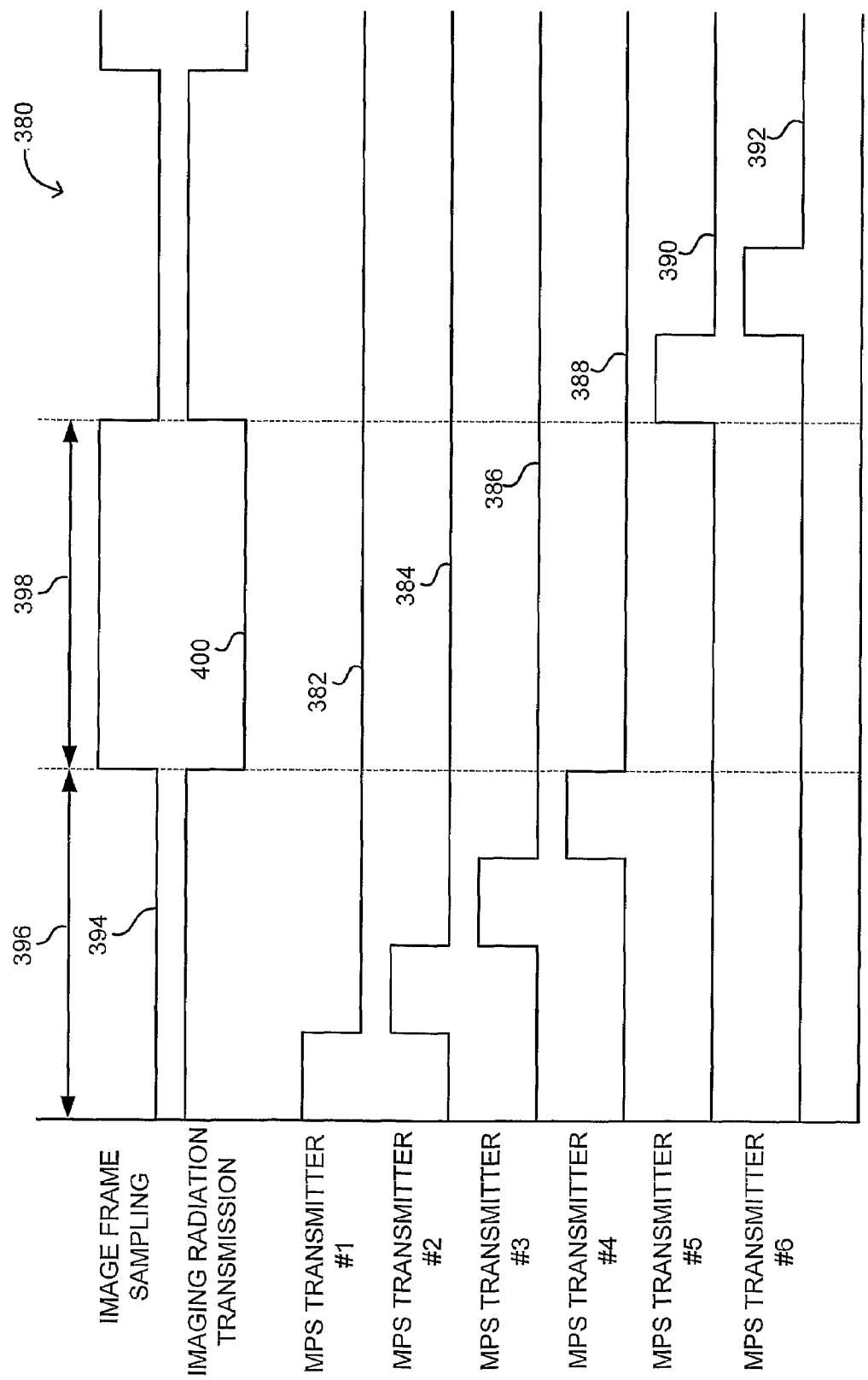
FIG. 11 is a schematic illustration of a timing diagram, in accordance with another embodiment of the disclosed technique.

Reference is now made to FIG. 11, which is a schematic illustration of timing diagram generally referenced 380 in accordance with another embodiment of the disclosed technique. In Timing diagram 380, six positioning radiation transmitters are employed by the MPS. Timing diagram 380 includes signals 382, 384, 386, 388, 390, 392, 394 and 400. Signal 382, 384, 386, 388, 390 and 392 are the timing signals associated with the operation of the positioning radiation transmitters. Signal 394 is associated with the image frame sampling. Signal 400 is the timing signal associated with the transmission of imaging radiation by imaging radiation transmitter 172 (FIG. 3).

During time period 396, medical imaging system transmits medical imaging radiation and does not sample an image frame. Thus, the positioning radiation transmitters can transmit. However, time period 396 is sufficient to operate only positioning radiation transmitters number 1, 2, 3 and 4. During time period 398 synchronizer disables the positioning radiation transmitters from transmitting. Furthermore, during time period 398, the medical imaging system samples an image frame and does not transmit imaging radiation. However, after the sampling of the image frame stops, the synchronizer enables positioning radiation transmitters to transmit, starting from positioning radiation transmitter number 5.

Figure 12:
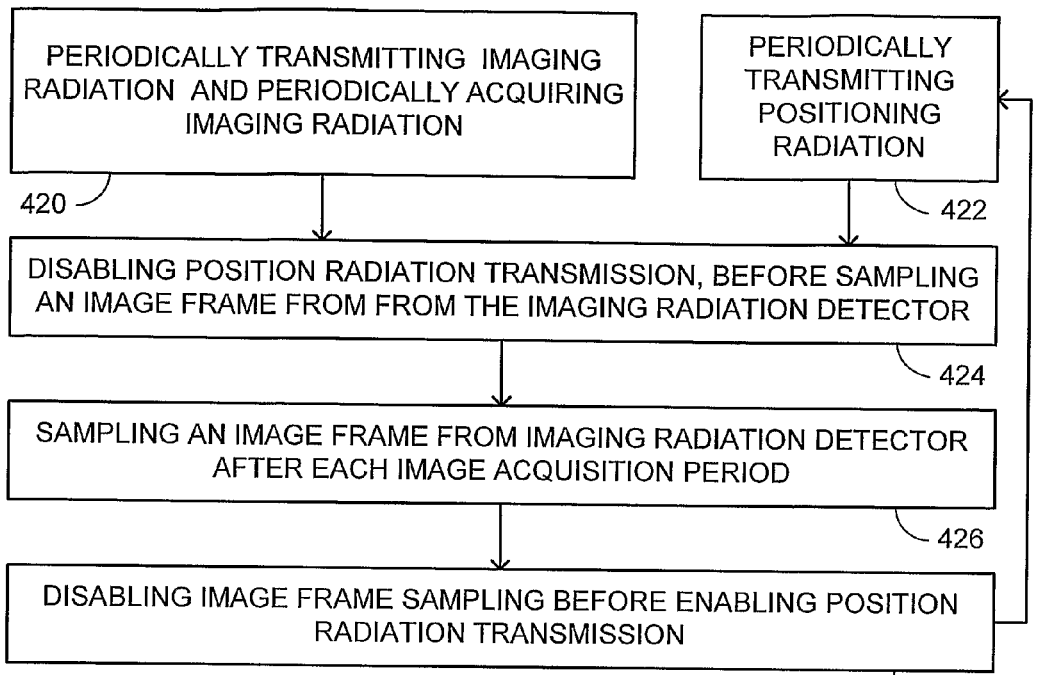
FIG. 12, which is a schematic illustration of a method for synchronizing system the operation of a medical position system with a medical imaging system operative in accordance with a further embodiment of the disclosed technique.

As mentioned above, according to a further embodiment of the disclosed technique, the transmission radiation transmission and the acquired image sampling are synchronized. Reference is now made to FIG. 12, which is a schematic illustration of a method for synchronizing system the operation of a medical position system with a medical imaging system operative in accordance with a further embodiment of the disclosed technique. In procedure 420, imaging radiation is periodically transmitted and imaging radiation is periodically acquired. With reference to FIG. 3, imaging radiation transmitter 172 periodically transmits imaging radiation and imaging radiation detector 176 periodically acquires imaging radiation. After procedure 420, the method proceeds to procedure 424. In procedure 422, position radiation is periodically transmitted. With reference to FIG. 3, position radiation transmitters 156, 158 and 160 periodically transmit position radiation.

In procedure 424, the position radiation transmission is disabled before sampling an image frame from the imaging radiation detector. The position radiation detector may interfere with the image frame sampling, thereby corrupting the image. With reference to FIG. 3, synchronizer 180 disables the image frame sampling before enabling the positioning radiation transmission.

In procedure 426, an image frame is sampled after each image acquisition period form the imaging radiation detector. The image frame forms an image on the display unit. With reference to FIG. 3, imaging detector 176 samples an image frame after each image acquisition period.

In procedure 428, image frame sampling is disabled before enabling position radiation transmission. With reference to FIG. 3, synchronizer 180 disables the image frame sampling. After procedure 430 the method returns to procedure 422.

Figure 13:
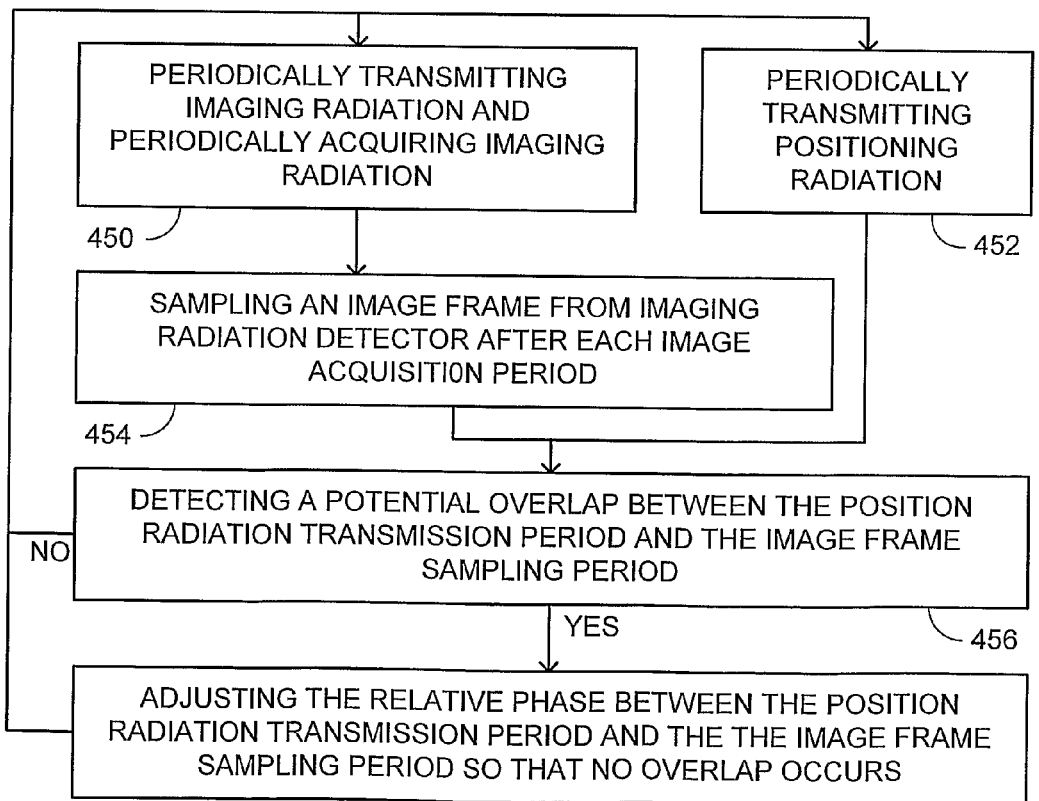
FIG. 13, which is a schematic illustration of a method for synchronizing the operation of an MPS with a medical imaging system, operative in accordance with another embodiment of the disclosed technique.

According to another embodiment of the disclosed technique, synchronization between the position radiation transmission and the image frame sampling is achieved by detecting the relative phase between the position radiation transmission period and the image frame sampling period, and adjusting this relative phase when necessary. Reference is now made to FIG. 13, which is a schematic illustration of a method for synchronizing the operation of an MPS with a medical imaging system, operative in accordance with another embodiment of the disclosed technique. In procedure 450, imaging radiation is periodically transmitted and imaging radiation is periodically acquired. With reference to FIG. 3, imaging radiation transmitter 172 periodically transmits imaging radiation and imaging radiation detector 176 periodically acquires imaging radiation. After procedure 450, the method proceeds to procedure 454. In procedure 452, positioning radiation is periodically transmitted while imaging radiation is acquired and while imaging radiation is periodically transmitted. With reference to FIG. 3, positioning radiation transmitters 156, 158, and 160 periodically transmit positioning radiation. After procedure 454, the method proceeds to procedure 458.

In procedure 454, an image frame is sampled from the imaging radiation detector after each position radiation acquisition period. With reference to FIG. 3, imaging detector 176 samples an image frame after each image acquisition period.

In procedure 456, a potential overlap between the imaging radiation transmission period and the image frame sampling period is detected. This potential overlap is detected according to a change in the relative phase between the two periods. The relative phase is defined as the difference between the imaging radiation non-sampling period and the positioning radiation transmission period. With reference to FIG. 4, the relative phase range 216 is the relative phase range in which the phase of either the image frame sampling period or the positioning radiation transmission period may change without the two transmission periods overlapping. When the combined relative phase drift of the image frame sampling period and the positioning radiation transmission period is larger than the relative phase range, then a potential overlap is detected and the method proceeds to procedure 458. When the relative phase drift of the image frame sampling period and the positioning radiation transmission period is at most equal to the relative phase range, then, no potential overlap is detected and the method proceeds to procedures 450 and 452. With reference to FIG. 3, synchronizer 180 detects a potential overlap an image frame sampling period and the positioning radiation transmission period.

In procedure 458, the relative phase between the image frame sampling period and the positioning radiation transmission period is adjusted so that no overlap occurs. With reference to FIG. 3, synchronizer 180 adjusts the relative phase between the image frame sampling period and the positioning radiation transmission period. After procedure 460, the method proceeds to procedure 450 and 452.

Figure 14:
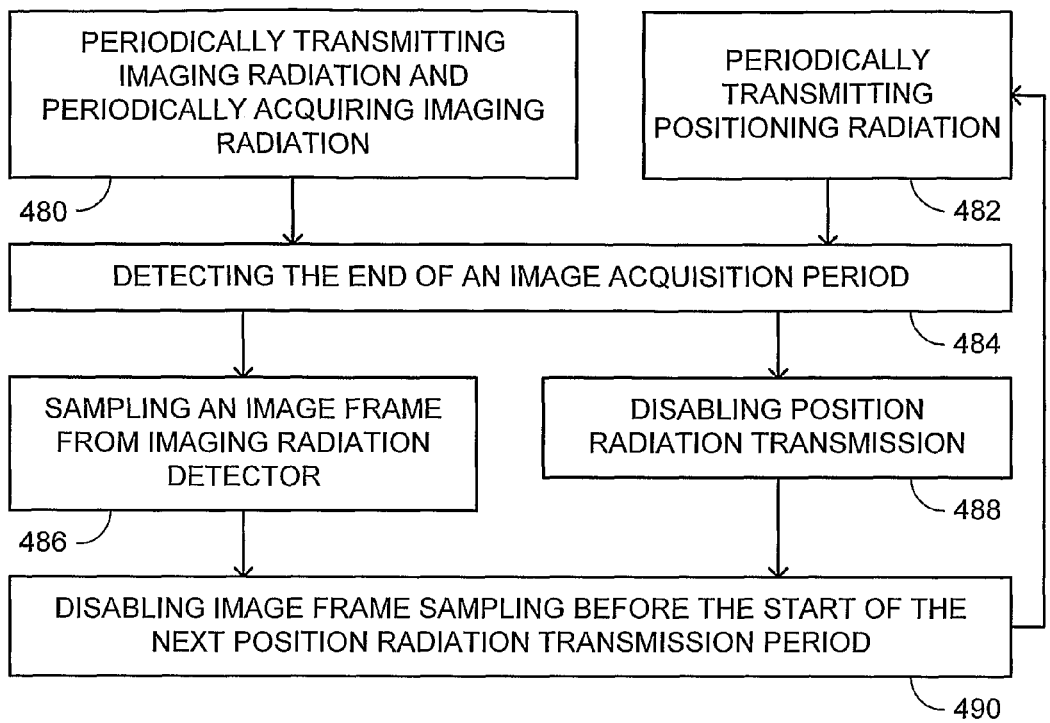
FIG. 14 which is a schematic illustration of a method for synchronizing the operation of an MPS with a medical imaging system, operative in accordance with a further embodiment of the disclosed technique.

According to a further embodiment of the disclosed technique, synchronization is achieved by disabling the position radiation transmission when the end of an image acquisition period is detected. The end of the image acquisition period marks the start of the image frame sampling period. Reference is now made to FIG. 14 which is a schematic illustration of a method for synchronizing the operation of an MPS with a medical imaging system, operative in accordance with a further embodiment of the disclosed technique. In procedure 480, imaging radiation is periodically transmitted and imaging radiation is periodically acquired. With reference to FIG. 3, imaging radiation transmitter 172 periodically transmits imaging radiation and imaging radiation detector 176 periodically acquires imaging radiation. After procedure 480, the method proceeds to procedure 484.

In procedure 482, positioning radiation is periodically transmitted while imaging radiation is acquired and while imaging radiation is periodically transmitted. With reference to FIG. 3, positioning radiation transmitters 156, 158, and 160 periodically transmit positioning radiation. After procedure 482, the method proceeds to procedure 484.

In procedure 484, the end of the image acquisition period is detected. With reference to FIG. 3, synchronizer 180 detects the end of the imaging acquisition period. After procedure 484, the method proceeds to procedures 486 and 488.

In procedure 486, the image frame is sampled from the imaging radiation detector. With reference to FIG. 3, imaging detector 176 samples the image frame after each image acquisition period.

In procedure 488, the position radiation transmission is disabled while the image frame is sampled. With reference to FIG. 3, synchronizer 180 disables positioning radiation transmitters 156, 158 and 160.

In procedure 490, the image frame sampling is disabled before the start of the next position radiation transmission period. With reference to FIG. 3, synchronizer 180 disables image frame sampling before the start of the next position radiation transmission period. After procedure 490 the method returns to procedure 484

Figure 15:
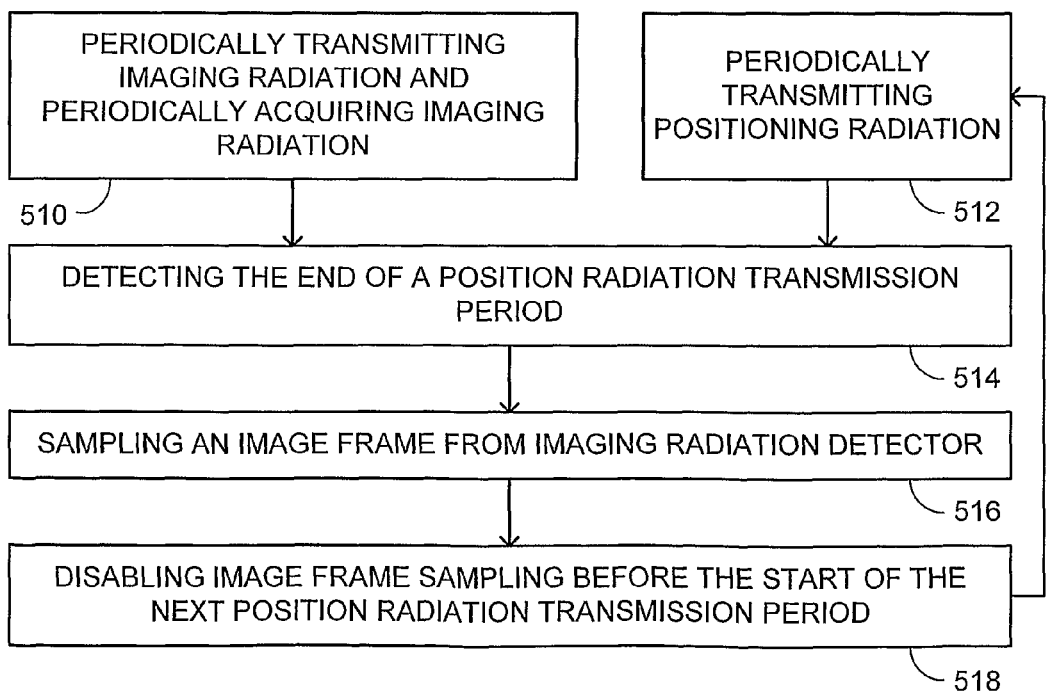
FIG. 15 which is a schematic illustration of a method for synchronizing the operation of an MPS with a medical imaging system, operative in accordance with another embodiment of the disclosed technique.

In accordance with another embodiment of the disclosed technique, synchronization is achieved by disabling the image frame sampling when the end of a position radiation transmission period is detected. FIG. 15 which is a schematic illustration of a method for synchronizing the operation of an MPS with a medical imaging system, operative in accordance with another embodiment of the disclosed technique. In procedure 510, imaging radiation is periodically transmitted and imaging radiation is periodically acquired. With reference to FIG. 3, imaging radiation transmitter 172 periodically transmit imaging radiation imaging radiation detector 176 periodically acquires imaging radiation. After procedure 510, the method proceeds to procedure 514.

In procedure 512, positioning radiation is periodically transmitted while imaging radiation is acquired and while imaging radiation is periodically transmitted. With reference to FIG. 3, positioning radiation transmitters 156, 158, and 160 periodically transmit positioning radiation. After procedure 5124, the method proceeds to procedure 514.

In procedure 516, the end of the position radiation transmission period is detected. With reference to FIG. 3, synchronizer 180 detects the end of the imaging acquisition period.

In procedure 516, the image frame is sampled from the imaging radiation detector. With reference to FIG. 3, imaging detector 176 samples the image frame after each image acquisition period.

In procedure 518, image frame sampling is disabled before the start of the next position radiation transmission period. With reference to FIG. 3, synchronizer 180 disables image frame samples before the start of the next position radiation transmission period. After procedure 518 the method returns to procedure 512.

It will be appreciated by persons skilled in the art that the disclosed technique is not limited to what has been particularly shown and described hereinabove. Rather the scope of the disclosed technique is defined only by the claims, which follow.

The invention claimed is:

1. In a medical apparatus including a medical imaging system and a medical position and navigation system (MPS), the medical imaging system including an imaging transmitter periodically emitting imaging radiation and a separate imaging detector having at least an imaging radiation acquisition mode of operation and a sampling mode of operation, the MPS including at least one MPS transmitter periodically transmitting MPS radiation and at least one MPS detector, with one of the at least one MPS transmitter and the at least one MPS detector being positionable within a body, said MPS radiation electromagnetically interfering with at least one of said modes of operation of said imaging detector, a device for eliminating interference to the imaging detector caused by positioning radiation, the device comprising:

a synchronizer configured to be coupled with said medical imaging system and with said MPS, wherein said synchronizer is configured to synchronize said imaging detector and said at least one MPS transmitter, so that said at least one MPS transmitter does not transmit during said at least one of said modes of operation of said imaging detector, wherein said at least one of said modes of operation of said imaging detector is said imaging radiation acquisition mode.

2. The device according to claim 1, wherein said at least one of said modes of operation of said imaging detector is said sampling mode.

3. A combined imaging and positioning apparatus comprising:

a medical imaging system, for obtaining a representation of the anatomy of a portion of a body, said medical imaging system including an imaging radiation transmitter for periodically transmitting imaging radiation and a separate imaging detector having at least an imaging radiation acquisition mode of operation and a sampling mode of operation;

a medical position and navigation system (MPS), said MPS including at least one MPS transmitter for transmitting MPS radiation, said MPS radiation electromagnetically interfering with at least one of said modes of operation of said imaging detector, and at least one MPS detector for detecting MPS radiation, with one of said at least one MPS transmitter and said at least one MPS detector being positionable within the body; and a synchronizer coupled with said medical imaging system and with said MPS, wherein said synchronizer is configured to synchronize said imaging detector and said at least one MPS transmitter, so that said at least one MPS transmitter does not transmit during said at least one of said modes of operation of said imaging detector, wherein said at least one of said modes of operation of said imaging detector is said imaging radiation acquisition mode.

4. The system according to claim 3, wherein said at least one of said modes of operation of said imaging detector is said sampling mode.

5. The apparatus according to claim 3, further including a display unit coupled with said medical imaging system and said medical positioning system, said display unit for displaying said representation of said anatomy in conjunction with the position of an object.

6. The system according to claim 5, wherein said medical imaging system further includes an imaging processor coupled with said imaging radiation transmitter, coupled with said imaging radiation detector, coupled with said display unit, and coupled with said synchronizer, said imaging processor for controlling the operation of said imaging radiation transmitter and said imaging radiation detector.

7. The system according to claim 5, wherein said MPS further includes a positioning processor coupled with said at least one MPS transmitter, coupled with said at least one MPS detector, coupled with said display unit, and coupled with said synchronizer, said positioning processor for controlling the operation of said at least one MPS transmitter and said at least one MPS detector.

8. The system according to claim 3, wherein said positioning radiation is electromagnetic.

9. The system according to claim 8, wherein said at least one MPS detector comprises at least one coil.

10. The system according to claim 8, wherein said at least one MPS transmitter comprises at least one coil.

11. The system according to claim 3, wherein said at least one MPS transmitter is in close proximity with said imaging detector and moves therewith, thereby maintaining registration between an MPS coordinate system associated with said MPS and with an imaging coordinate system associated with said imaging system.

12. The device according to claim 3, wherein said imaging detector comprises electromagnetic shielding.

13. The system according to claim 5, wherein said object is a catheter.

14. The system according to claim 13, wherein at least one of said at least one MPS detector is fitted on a distal end of said catheter.

* * * * *